United States Patent [19]

Gane et al.

[11] 4,205,190
[45] May 27, 1980

[54] PROCESS FOR THE HYDROCARBONYLATION OF METHANOL TO ETHANOL IN THE PRESENCE OF ADDED OXYGEN-CONTAINING ORGANIC COMPOUNDS

[75] Inventors: Brian R. Gane, Weybridge; David G. Stewart, Epsom, both of England

[73] Assignee: The British Petroleum Company Limited, London, England

[21] Appl. No.: 11,190

[22] Filed: Feb. 12, 1979

[30] Foreign Application Priority Data

Feb. 17, 1978 [GB] United Kingdom ............... 06291/78

[51] Int. Cl.$^2$ .............................................. C07C 31/08
[52] U.S. Cl. ..................................................... 568/902
[58] Field of Search ......................................... 568/902

[56] References Cited

U.S. PATENT DOCUMENTS

| | | | |
|---|---|---|---|
| 2,623,906 | 12/1952 | Gresham | 568/902 |
| 3,248,432 | 4/1966 | Riley et al. | 568/902 |
| 3,285,948 | 11/1966 | Butter | 568/902 |
| 4,133,966 | 1/1979 | Pretzer et al. | 568/902 |
| 4,150,246 | 4/1979 | Taylor | 568/902 |

FOREIGN PATENT DOCUMENTS 951506 3/1964 United Kingdom ..................... 568/902

OTHER PUBLICATIONS

Wender et al., "Science," vol. 113 (1951), pp. 206–207.

*Primary Examiner*—Joseph E. Evans
*Attorney, Agent, or Firm*—Brooks, Haidt, Haffner & Delahunty

[57] ABSTRACT

Ethanol is produced by reacting methanol with carbon monoxide and hydrogen at temperatures in the range 150° to 250° C. and pressures greater than 100 bar in the presence of a cobalt catalyst and an additive which is miscible with methanol containing up to 20% w/w water, which additive is an alcohol, an aldehyde, a ketone or an ether. Particular additives are n-propanol, n-butanol, acetone, acetaldehyde, 1,4-dioxane, tetrahydrofuran, di-n-propylether and diphenyl ether. Optionally the catalyst is promoted with iodine or bromine or preferably both iodine or bromine and an organo-phosphorous compound. Other additives such as non-polar solvents, acids and derivatives thereof and inert liquids can be incorporated in the reaction mixture.

12 Claims, No Drawings

PROCESS FOR THE HYDROCARBONYLATION OF METHANOL TO ETHANOL IN THE PRESENCE OF ADDED OXYGEN-CONTAINING ORGANIC COMPOUNDS

The present invention relates to the production of ethanol from methanol and synthesis gas (mixtures of carbon monoxide and hydrogen) in the presence of a cobalt-containing catalyst.

Ethanol is a valuable industrial product which is generally manufactured either by fermentation of natural products, eg molasses or by hydration of ethylene in the presence of an acid catalyst, such as phosphoric acid. The rapidly dwindling reserves of crude oil from which ethylene is derived and the associated need to utilise fully the remaining natural resources such as coal and the vast amounts of gases, eg the methane potentially available from the exploitation of North Sea oilfields, has stimulated researchers to investigate other routes to ethanol utilising these materials as feedstocks. Both coal and methane gas can be converted into synthesis gas (CO+H$_2$), which in turn can be reacted to form methanol, which can be further reacted with carbon monoxide and hydrogen under appropriate conditions to form ethanol.

It has long been known that methanol can be hydrocarbonylated with hydrogen and carbon monoxide to ethanol in the presence of a water soluble cobalt catalyst at high temperatures and pressures. The course of this reaction can be represented by the following equation:

$$CH_3OH + CO + 2H_2 \rightarrow C_2H_5OH + H_2O$$

Thus in a paper published in Science 113, 206 (1951) Wender, Friedel and Orchin reported that methanol was reacted with synthesis gas (1H$_2$:1CO) in the presence of dicobalt octacarbonyl as catalyst to produce methyl formate (2%), methyl acetate (9.0%), ethyl alcohol (38.3%), ethyl acetate (6.3%), propyl alcohol (4.7%), butyl alcohol (0.09%), methane (8.5%), propyl acetate (0.1%) and a small amount of unidentified product, the total conversion of methanol being 76.4% over a reaction period of eight hours.

The problem with this and the majority of prior art processes is that they produce large amounts of by-products such as esters, and acids in addition to ethanol.

We have found that the total realisable yield and selectivity to ethanol, as hereinafter defined, can also be increased by the addition of alcohols, aldehydes, ketones and ethers which are miscible, under normal conditions of temperature and pressure, with methanol containing up to 20% w/w water. In the context of the present specification a miscible alcohol, aldehyde, ketone or ether is one which is not capable of forming a separate phase in the presence of methanol containing up to 20% w/w water under normal conditions of temperature and pressure.

By total realisable yield of ethanol within the context of the present specification is meant the yield of free ethanol plus the yield of ethanol realisable by the hydrolysis of ethanol-yielding esters (eg ethyl acetate). In the same way, by the total methanol fed or in the product is meant the free methanol in the feed or in the product plus the methanol realisable by the hydrolysis of methanol-yielding esters (eg methyl acetate).

Thus, the % Molar Yield of Realisable Ethanol $$= \frac{\text{Moles of methanol converted into realisable ethanol}}{\text{Total moles of methanol fed}} \times 100$$

and the % Molar Selectivity to Realisable Ethanol $$= \frac{\text{Moles of methanol converted into realisable ethanol}}{\text{Total moles of methanol converted}} \times 100$$

By the yield of realisable acetic acid is meant the yield of free acetic acid plus the yield of acetic acid realisable by the hydrolysis of acetic acid-yielding esters (eg methyl acetate). In calculating the yield it is assumed that all the acetic acid is derived from methanol and synthesis gas and no account is taken of acetic acid derived from cobalt acetate, when this is added as catalyst.

Thus, the % Molar Yield of Realisable Acetic Acid $$= \frac{\text{Moles of methanol converted into realisable acetic acid}}{\text{Total moles of methanol fed}} \times 100$$

% Methanol conversion =
$$\frac{\text{Total moles of methanol converted}}{\text{Total moles of methanol fed}} \times 100$$

Thus the present invention provides a process for the production of ethanol which process comprises contacting a mixture of methanol and synthesis gas at elevated temperature and pressure with a cobalt-containing catalyst in the presence of an added oxygen-containing organic compound miscible, under normal conditions of temperature and pressure, with methanol containing up to 20% w/w water comprising an aldehyde, a ketone, an alcohol or an ether or a mixture of two or more such compounds.

Methanol is a readily available industrial product. It is generally manufactured on an industrial scale from synthesis gas. Whilst it is preferred that the methanol be substantially pure, the presence of small amounts of certain impurities, in addition to aldehydes, ketones, alcohols and ethers can be tolerated. The methanol may however contain up to 50% by weight of water.

Mixtures of the gases hydrogen and carbon monoxide are abundantly available in the form of synthesis gas. Methods for preparing synthesis gas are well-known in the art and usually involve the partial oxidation of a carbonaceous substance, eg coal. Alternatively synthesis gas may be prepared, for example, by the catalytic steam reforming of methane. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

The cobalt-containing catalyst may be added directly, eg in the form of dicobalt octacarbonyl, which may be prepared by heating an anhydrous cobalt compound in a non-aqueous solvent at a temperature greater than 100° C. and in a superatmosphere of carbon monoxide and hydrogen. Alternatively the cobalt-containing catalyst may be formed 'in situ' under the prevailing reaction conditions by simply adding a source of cobalt to the initial reaction mixture. Any source of cobalt which will react with carbon monoxide and hydrogen to yield a cobalt carbonyl or cobalt carbonyl/hydride complex under the prevailing reaction conditions may be employed. Cobalt is preferably employed in the ionic form but the use of cobalt metal to react in situ to form ionic cobalt which then further reacts to form the desired cobalt complex is within the scope of the present invention. Typical sources of cobalt are, for example compounds such as cobalt acetate, cobalt formate, cobalt propionate and the like, which under the reaction conditions form carbonyl or carbonyl/hydride complexes. The amount of cobalt catalyst present may suitably be sufficient to provide a cobalt to methanol molar ratio in the range 1:10 to 1:1000, preferably 1:40 to 1:800.

In addition to the catalyst one or more promoters may optionally be incorporated in the reaction mixture. Suitable promoters include iodine, bromine and certain organo-phosphorus compounds. Preferably the cobalt catalyst is promoted with iodine, even more preferably with a combination of both iodine or bromine, preferably iodine, and an organo-phosphorus compound. The iodide or bromide may be added either in ionic form, eg as cobalt iodide or cobalt bromide, or as molecular iodine ($I_2$) or bromine ($Br_2$). Furthermore the iodide or bromide may be added as an alkyl or aryl iodide or bromide, preferably methyl iodide. However the iodide or bromide may also be added in ionic form utilising cations which are inert with regard to the hydrocarbonylation reaction. Typical of the inert form is potassium iodide or bromide, sodium iodide or bromide and lithium iodide or bromide. The molar ratio of cobalt to iodine or bromine may suitably be in the range 1:3 to 10:1, preferably 1:1 to 5:1. Suitable organo-phosphorus compounds are compounds having the formula:

(I)

wherein X is phosphorus and A, B and C are individually monovalent organic radicals or any two of A, B and C together form an organic divalent cyclic ring system bonded to the X atom. A class of compound having the formula (I) found to be particularly useful in the process of the present invention are phosphines having the general formula:

$R_3P$ (II)

wherein R independently is an organo group containing from 1 to 20 carbon atoms, is preferably free from aliphatic carbon-carbon unsaturation, and is bonded to the phosphorus atom by a carbon/phosphorus bond. The organo group R in the phosphine of formula (II) is preferably a hydrocarbyl group which may be a saturated aliphatic, a saturated cycloaliphatic, an aromatic, a substituted saturated aliphatic, a substituted saturated cycloaliphatic or a substituted aromatic group of which the unsubstituted saturated and aromatic groups are preferred. The substituents are preferably free from aliphatic carbon-carbon unsaturation and may contain, besides atoms of carbon and hydrogen, other atoms, such as oxygen, sulphur and halogen, in particular halogen of atomic number from 9 to 35, provided that such atoms are not directly bonded to phosphorus. Illustrative of suitable saturated aliphatic R groups are hydrocarbyl R groups such as methyl, ethyl, propyl, isopropyl, butyl, isoctyl, decyl, dodecyl, octadecyl, cyclohexyl, cyclopentyl, 3,4-dimethyl cyclopentyl, cyclooctyl, benzyl and $\beta$-phenylethyl. Aromatic R groups include hydrocarbyl aromatic groups such as phenyl, tolyl, xylyl, p-ethylphenyl, p-tert-butylphenyl, m-octylphenyl, 2,4-diethylphenyl, p-phenylphenyl, m-benzylphenyl and 2,4,6-trimethylphenyl. In the compound of formula (II) the R moieties may be the same or different, although for economic reasons they are preferably identical. Exemplary compounds of formula (II) are triethyl phosphine, tributylphosphine, tricyclohexylphosphine, triphenylphosphine, tris (4-tolyl) phosphine, tris (3-chlorophenyl) phosphine, diphenylhexylphosphine, dibutyloctadecylphosphine, tribenzylphosphine, cyclohexyldibutylphosphine and the like. Preferred compounds are triethylphosphine, tri-n-butylphosphine, tricyclohexylphosphine, tri-t-butylphosphine and triphenylphosphine. The molar ratio of cobalt to compound of formula (I) may be in the range of from 2:1 to 1:10, preferably from 1:1 to 1:5. At the higher reaction temperatures it may also be advantageous to include in the reaction mixture small amounts of a catalyst stabiliser. Stabilisers which may be used, for example, include those disclosed in U.S. Pat. No. 3,931,332 to Chevron Research Company.

Whilst it is appreciated that oxygen-containing organic compounds comprising aldehydes, ketones, alcohols and ethers may be formed as by-products during the course of the hydrocarbonylation reaction the invention resides in the addition of such a compound or a mixture thereof to the reaction mixture. It is found that by so-doing the amount of unwanted side reaction is reduced, with the attendant consequence that the total selectivity to ethanol is increased. Preferably the compound is one which exists mainly in the form of a liquid under the reaction conditions chosen. Certain of the compounds falling within the scope of the present invention may be reduced or hydrolysed under the reaction conditions employed. For example, certain aldehydes may be reduced to alcohols and certain ethers hydrolysed to alcohols. Whilst such compounds may be used in the process of the invention it is preferred to add compounds which are not so affected. The alcohol added is preferably an aliphatic alcohol. Suitable aliphatic alcohols include n-propanol and n-butanol. The ketone added is preferably an aliphatic ketone. Suitable aliphatic ketones include acetone. The aldehyde added is preferably an aliphatic aldehyde. Suitable aliphatic aldehydes include acetaldehyde. Preferably the added compound is an aliphatic, alicyclic or aromatic ether. Suitable ethers include 1,4-dioxane, tetrahydrofuran, di-n-propyl ether and diphenyl ether. Preferably the ether is 1,4-dioxane. The compound or mixtures of compounds may be added in an amount such that the molar ratio of methanol to the compound or mixture of compounds contacted with the catalyst is in the range from 20:1 to 1:3, preferably from 10:1 to 1:1. It is thought that the added oxygen-containing organic compounds are effective because they are capable of forming a co-ordinate linkage between the lone pair of electrons on the oxygen atom and the incomplete electron shell of the cobalt atom thereby directing the reaction mechanism, in some manner, towards the formation of ethanol but we do not intend to be bound in any way by any particular theory.

In addition to the oxygen-containing organic compound essential to the invention there may also be added non polar solvents such as alkanes, benzene and alkyl-substituted benzenes, as disclosed in U.S. application Ser. No. 585,276, now abandoned.

Furthermore there may also be added one or more acids and derivatives thereof having the formula:

wherein the substituent R is a hydrocarbyl group or an oxygen-containing hydrocarbyl group and the substituent X is the group OR$^1$ in which R$^1$ is independently a hydrogen atom, a hydrocarbyl group or an oxygen-containing hydrocarbyl group or X is the group —O—CO—R$^2$ wherein R$^2$ is independently a hydrocarbyl group or an oxygen-containing hydrocarbyl group as described in our copending application No. 908,060 filed on May 22, 1978, now abandoned in favor of Ser. No. 052,006 filed on June 25, 1979. Preferred compounds having the formula (III) are acetic acid and methyl acetate. The compound of formula (III) may be added in an amount such that the molar ratio of the compound to free methanol in the reaction mixture can be as high as 1.5:1, but is normally in the range 0.1:1 to 0.7:1.

Our copending application No. 957,700 filed on Nov. 6, 1978 relates to a process for the production of ethanol which process comprises reacting, at elevated temperature and pressure, methanol with hydrogen and carbon monoxide in the presence of an inert liquid and a catalyst comprising cobalt, an iodide or a bromide and a compound having the formula:

wherein X is nitrogen or phosphorus and A, B and C are individually monovalent organic radicals, or X is phosphorus and any two of A, B and C together form an organic divalent cyclic ring system bonded to the X atom, or X is nitrogen and all of A, B and C together form an organic trivalent cyclic ring system bonded to the X atom. The term inert liquid as used in that specification means a compound which does not poison or otherwise adversely affect the catalyst, is mainly in liquid form under the conditions of the reaction, is capable of forming a separate phase in the presence of methanol containing up to 20% w/w water under normal conditions of temperature and pressure and is further characterised by having in its molecular structure one or more atoms other than carbon and hydrogen. Inert liquids, as defined in that application, may be used as supplemental additives in the process of the present invention. The inert liquid may be, for example, an aryl halide, an ether, a thiophene, a long chain acid, an aromatic acid or a silicone oil. Preferably the inert liquid is chorobenzene, decanoic acid, a polydimethylsiloxane fluid or a methyl phenyl silicone fluid. The molar ratio of methanol to the inert liquid can be varied within wide limits, eg from 30:1 to 1:10, preferably from 25:1 to 1:2. In the case of silicone oils for which the molecular weight is not known with any degree of certainty the ratio of the volume added to the volume of methanol fed may be in the range from 0.05:1 to 50:1, preferably from 0.1:1 to 5:1.

The mixture of synthesis gas and methanol is suitably contacted with the catalyst at an elevated temperature in the range of from 150° to 250° C., preferably from 175° to 230° C. and at an elevated pressure greater than 100, preferably 140 to 300 bar. At temperatures in excess of 200° C. and/or at low pressures it may be necessary to use a catalyst stabiliser as hereinbefore described.

The molar ratio of methanol to synthesis gas fed may be in the range of from 10:1 to 1:20, preferably from 2:1 to 1:5. The molar ratio of carbon monoxide to hydrogen in the synthesis gas fed may suitably be in the range 2:1 to 1:3. In the presence of combinations of organo-phosphorus compounds having the formula (I) and iodine or bromine it is advantageous to employ molar ratios of carbon monoxide to hydrogen in the range 1:1 to 2:5, preferably 1:2. However in the absence of organo-phosphorus compounds there is no advantage to be derived from using excess hydrogen in the synthesis gas fed and in consequence molar ratios of carbon monoxide to hydrogen are preferably in the range 3:2 to 2:3 even more preferably 1:1. Methods for adjusting the molar ratio of carbon monoxide to hydrogen are well-known in the art.

The process may be carried out batchwise or continuously, continuous operation being preferred. The process may be carried out continuously for example by feeding methanol and synthesis gas to a reactor containing the catalyst and the added compound, removing from the reactor a liquid product containing ethanol, oxygen-containing organic compounds, by-products, unchanged methanol, catalyst and unreacted synthesis gas, separating the synthesis gas which may be recycled to the reactor, removing light ends, separating the product containing ethanol and by-products from the catalyst and thereafter recovering ethanol from the by-products, there being recycled to the reactor the catalyst, methanol and oxygen-containing organic compounds. Other reaction by-products particularly those which can act as precursors for the formation of ethanol such as acetaldehyde and 1,1-dimethoxyethane may also be recycled to the reactor with advantage. It may be necessary to feed from time to time further catalyst.

The residence time may suitably be up to 8 hours, but is preferably in the range of from 10 to 180 minutes. Within the context of the specification the residence time for batchwise operation is that time during which the reactor is at the specified reaction temperature. When the process is operated continuously the residence time is calculated as follows:

$$\text{Residence Time (Hours)} = \frac{\text{Volume of the reactor occupied by the liquid phase at } STP \text{ (liters)}}{\text{Total flow of liquid into the reactor (liters/hour at } STP\text{)}}$$

The following Examples will now serve to illustrate the process of the invention.

EXAMPLE 1

A stainless steel, magnetically stirred autoclave equipped for pressurised reactions was charged with methanol (6.0 moles) containing cobalt acetate tetrahydrate (75×10$^{-3}$ moles). To this mixture was further added 1,4-dioxane (0.9 moles). The system was purged with nitrogen and then pressurised to 200 bars with a mixture of carbon monoxide and hydrogen (1:1 molar). The reactor temperature was then raised to 185° C. and maintained at this value for 2 hours. When heating was commenced the pressure in the reactor rose above 200 bars and then began to decrease as the reaction started. During the course of the reaction, whenever the pressure in the autoclave fell to 140 bars a fresh charge of carbon monoxide and hydrogen (1:1 molar mixture) was added thereby increasing the reactor pressure to 200 bars. After two hours at 185° C. the autoclave was allowed to cool and the reaction product was analysed. The amounts of reactants are given in Table 1A and the results are given in Table 1B.

Comparison Test A

The procedure described in Example 1 was followed using the reactants in the concentrations shown in Table 1A and with the results shown in Table 1B.

This is not an example according to the invention because no oxygen-containing organic solvent was added.

EXAMPLE 2

The procedure described in Example 1 was followed except that the amount of 1,4-dioxane added was increased to 1.35 moles, the amount of catalyst was reduced to $56.3 \times 10^{-3}$ moles and the amount of methanol was reduced to 4.5 moles.

The amounts of reactants are shown in Table 1A and the results obtained are given in Table 1B.

EXAMPLE 3

The procedure described in Example 1 was followed except that tetrahydrofuran (0.9 moles) was added in place of 1,4-dioxane (0.9 moles).

The amounts of reactants are shown in Table 1A and the results obtained are given in Table 1B.

EXAMPLE 4

The procedure of Example 1 was followed except that tetrahydrofuran (1.5 moles) was added in place of 1,4-dioxane (0.9 moles), the amount of catalyst was reduced to $62.5 \times 10^{-3}$ moles and the amount of methanol was reduced to 5.0 moles.

The amounts of reactants are shown in Table 1A and the results obtained are given in Table 1B.

EXAMPLE 5

The procedure of Example 1 was followed except that tetrahydrofuran (2.7 moles) was added in place of 1,4-dioxane (0.9 moles), the amount of catalyst was reduced to $33.8 \times 10^{-3}$ moles and the amount of methanol was reduced to 2.7 moles.

The amounts of reactants are shown in Table 1A and the results obtained are given in Table 1B.

EXAMPLE 6

The procedure of Example 1 was followed except that di-n-propyl ether (0.65 moles) was added in place of 1,4-dioxane (0.9 moles), the amount of catalyst was reduced to $53.8 \times 10^{-3}$ moles and the amount of methanol was reduced to 4.3 moles.

The amounts of reactants are shown in Table 1A and the results obtained are given in Table 1B.

EXAMPLE 7

The procedure of Example 1 was followed except that diphenyl ether (0.675 moles) was added in place of 1,4-dioxane (0.9 moles), the amount of catalyst was reduced to $56.3 \times 10^{-3}$ moles and the amount of methanol was reduced to 4.5 moles.

The amount of reactants are shown in Table 1A and the results obtained are given in Table 1B.

Examination of Table 1B shows that the addition of an oxygen-containing organic compound in the form of an ether to the unpromoted cobalt-catalysed reaction significantly increases the % molar selectivity and yield to realisable ethanol without substantially affecting the % methanol conversion (Examples 1 to 7).

EXAMPLE 8

The procedure of Example 1 was followed except that diphenyl ether (0.675 moles) was added in place of 1,4-dioxane (0.9 moles) and the amount of methanol was reduced to 4.5 moles. Furthermore only $56.3 \times 10^{-3}$ moles cobalt acetate tetrahydrate was added and a promoter, iodine was added in an amount of $28.1 \times 10^{-3}$ moles.

The amounts of reactants are shown in Table 2A and the results obtained are given in Table 2B.

EXAMPLE 9

Example 8 was repeated except that diphenyl ether (0.675 moles) was replaced by 1,4-dioxane (1.35 moles).

The amounts of reactants are shown in Table 2A and the results obtained are given in Table 2B.

EXAMPLE 10

Example 9 was repeated except that an acid derivative, methyl acetate, (1.0 moles) was added in addition to 1,4-dioxane (1.2 moles). Otherwise the amounts of reactants are as given in Table 2A. The results obtained are given in Table 2B.

Comparison Test B

Example 8 was repeated using the reactants in the concentrations shown in Table 2A and with the results shown in Table 2B.

This is not an example according to the invention because no oxygen-containing organic solvent was added.

Examination of Table 2 shows that the addition of an oxygen-containing organic compound in the form of an ether to the reaction promoted by iodine not only increases the % molar selectivity and yield to realisable ethanol but also increases significantly the % methanol conversion.

EXAMPLE 11

The procedure of Example 1 was followed except that acetone (0.9 moles) was added in place of 1,4-dioxane (0.9 moles).

The amounts of reactants are given in Table 3A and the results obtained are given in Table 3B.

EXAMPLE 12

The procedure of Example 1 was followed except that acetone (1.5 moles) was added in place of 1,4-dioxane (0.9 moles), the amount of catalyst was reduced to $62.5 \times 10^{-3}$ moles and the amount of methanol was reduced to 5 moles.

The amounts of reactants are given in Table 3A and the results obtained are given in Table 3B.

EXAMPLE 13

The procedure of Example 1 was followed except that n-propanol (0.9 moles) was added in place of 1,4-dioxane (0.9 moles).

The amounts of reactants are given in Table 3A and the results obtained are given in Table 3B.

EXAMPLE 14

The procedure of Example 1 was followed except that n-butanol (2.7 moles) was added in place of 1,4-dioxane (0.9 moles), the amount of catalyst was reduced to $33.8 \times 10^{-3}$ moles and the amount of methanol was reduced to 2.7 moles.

The amounts of reactants are given in Table 3A and the results obtained are given in Table 3B.

Comparison Test C

The procedure of Example 1 was followed except that no oxygen-containing organic solvent was added, the amount of catalyst was reduced to $43.8 \times 10^{-3}$ moles and the amount of methanol was reduced to 3.5 moles. However, a solvent, octane (1.17 moles), was added.

The amounts of reactants are given in Table 3A and the results obtained are given in Table 3B.

This is not an example according to the invention because no oxygen-containing organic solvent was added.

Examination of Tables 1 and 3 shows that the addition of an oxygen-containing organic solvent to the unpromoted reaction increases the % molar selectivity and yield to realisable ethanol, though acetone, n-propanol and n-butanol do not appear to be as effective as the ethers.

Comparison Test D

The procedure of Example 1 was followed except that iodine ($12.6 \times 10^{-3}$ moles) and triphenylphosphine ($43.7 \times 10^{-3}$ moles) were added to the reaction mixture, whilst 1,4-dioxane was not included. The reaction temperature was 205° C.

The amounts of reactants are given in Table 4A and the results obtained are given in Table 4B.

This is not an example according to the invention because no oxygen-containing organic solvent was added.

EXAMPLE 15

The procedure of Comparison Test D was followed except acetone (0.15 moles), an oxygen-containing organic compound, was added to the reaction mixture.

The amounts of reactants are given in Table 4A and the results obtained are given in Table 4B.

EXAMPLE 16

The procedure of Comparison Test D was followed except that it was carried out on a larger scale and acetone (2.37 moles) was added to the reaction mixture. A higher concentration of acetone was used in this Example as compared to Example 15.

The amounts of reactants are given in Table 4A and the results obtained are given in Table 4B.

Comparison Test E

A stainless steel, magnetically-stirred autoclave equipped for pressurised reactions was charged under nitrogen with methanol (1.80 mole) containing cobalt acetate tetrahydrate (0.0225 mole), iodine (0.0113 mole) and triphenyl phosphine (0.0393 mole). The system was purged with nitrogen, then pressurised to 120 bars (roughly equivalent to a pressure of 200 bars at 190° C.) with a mixture of carbon monoxide and hydrogen (1:2 molar). The reactor temperature was then raised to 190° C. and maintained at this temperature for two hours. When heating was started the pressure in the reactor rose above 120 bars. As soon as the reaction commenced the rate of increase in the pressure began to decrease. It was therefore necessary to make periodic injections of carbon monoxide and hydrogen (1:2 molar mixture) to compensate for the gas consumed by the reaction and maintain the rate of pressure increase in accord with achieving a pressure of 200 bars at 190° C. When the pressure reached 200 bars it was maintained at that value throughout the reaction by continually feeding fresh carbon monoxide and hydrogen (1:2 molar mixture) to the autoclave. After two hours at 190° C. the autoclave was allowed to cool and the reaction product was analysed. The amounts of reactants are given in Table 4A and the results are given in Table 4B.

This is not an example according to the present invention because no oxygen-containing organic solvent was added.

EXAMPLE 17

The procedure of Comparison Test E was followed except that an oxygen-containing organic solvent, acetone (0.145 moles), was added to the reaction mixture.

The amounts of reactants are given in Table 4A and the results are given in Table 4B.

Examples 15 to 17 demonstrate that the addition of acetone, an oxygen-containing organic compound, to the reaction catalysed by cobalt and promoted with a combination of iodine and triphenyl phosphine improves the ethanol yield by increasing methanol conversion and slightly increasing reaction selectivity.

Example 17 demonstrates the additional benefit associated with using a hydrogen to carbon monoxide molar ratio of 2:1 in the presence of triphenylphosphine and iodine as promoters. The higher ratio results in a considerable reduction in the yield of realisable acetic acid.

TABLE 1A

| | REACTOR FEED | | |
|---|---|---|---|
| Example (a) | MeOH (moles) (b) | Oxygen-containing organic compound (moles) (c) | Catalyst components (moles × $10^{-3}$) (d) |
| Comp Test A | 8.0 | None | Co(OAc)$_2$4H$_2$O (100) |
| 1 | 6.0 | 1,4 Dioxane (0.9) | Co(OAc)$_2$4H$_2$O (75) |
| 2 | 4.5 | 1,4 Dioxane (1.35) | Co(OAc)$_2$4H$_2$O (56.3) |
| 3 | 6.0 | Tetrahydrofuran (0.9) | Co(OAc)$_2$4H$_2$O (75) |
| 4 | 5.0 | Tetrahydrofuran (1.5) | Co(OAc)$_2$4H$_2$O (62.5) |
| 5 | 2.7 | Tetrahydrofuran (2.7) | Co(OAc)$_2$4H$_2$O (33.8) |
| 6 | 4.3 | Di-n-propylether (0.65) | Co(OAc)$_2$4H$_2$O (53.8) |
| 7 | 4.5 | Diphenylether (0.675) | Co(OAc)$_2$4H$_2$O (56.3) |

TABLE 1B

| Example (e) | Realisable EtOH (f) | Realisable CH3COOH (g) | Dimethyl acetal* (h) | CH3CHO (i) | Ethers ** (j) | n-PrOH + n-BuOH (k) | % Molar yield CH4 + CO2 *** (l) | % Molar selectivity to realis' EtOH (m) | % MeOH conversion (n) |
|---|---|---|---|---|---|---|---|---|---|
| Comp Test A | 14.4 | 5.9 | 3.3 | <1 | 3.0 | 1.3 | 5.9 | 39.1 | 36.8 |
| 1 | 17.3 | 6.6 | 4.6 | <1 | 2.4 | 1.4 | 7.2 | 54.9 | 31.5 |
| 2 | 20.1 | 5.2 | 3.9 | <1 | 2.0 | 1.2 | 6.2 | 56.9 | 35.3 |
| 3 | 18.3 | 7.9 | 3.3 | <1 | 2.5 | 2.9+ | 6.3 | 55.1 | 33.2 |
| 4 | 20.3 | 7.6 | 2.3 | <1 | 2.6 | 5.2+ | 6.2 | 57.3 | 35.4 |
| 5 | 25.5 | 5.3 | 2.9 | < | 1.0 | 14.9+ | 3.3 | 72.6 | 35.1 |
| 6 | 19.0 | 5.5 | 1.9 | <1 | 2.4 | 5.7+ | 5.3 | 45.7 | 41.6 |
| 7 | 17.2 | 6.6 | 4.2 | <1 | 2.4 | 1.7 | 6.0 | 45.7 | 37.6 |

*Dimethyl acetal is 1,1 dimethyoxyethane
**Ethers are dimethyl ether + ethyl methyl ether
*** The percentage molar yield of methane plus carbon dioxide (ie $CH_4 + CO_2$) is calculated on the carbon monoxide fed to the reactor
+No allowance has been made in these figures for decomposition of the tetrahydrofuran and di-n-propyl ether to butanol and propanol respectively

TABLE 2A

| (a) | (b) | (c) | (d) | |
|---|---|---|---|---|
| Comp Test B | 2.0 | None | Co(OAc)2 4H2O | (25) |
| | | | I2 | (12.5) |
| 8 | 4.5 | Diphenylether 0.675 | Co(OAc)2 4H2O | (56.3) |
| | | | I2 | (28.1) |
| 9 | 4.5 | 1,4-Dioxane 1.35 | Co(OAc)2 4H2O | (56.3) |
| | | | I2 | (28.1) |
| 10 | 3.0 +Methyl acetate (1.0) | 1,4-Dioxane 1.2 | Co(OAc)2 4H2O | (50) |
| | | | I2 | (25) |

TABLE 2B

| (e) | (f) | (g) | (h) | (i) | (j) | (k) | (l) | (m) | (n) |
|---|---|---|---|---|---|---|---|---|---|
| Comp Test B | 16.6 | 11.0 | 4.9 | 1.1 | 1.1 | <1 | 6.8 | 36.9 | 45.0 |
| 8 | 22.6 | 9.0 | 7.2 | 1.7 | 1.5 | 2.4 | 6.7 | 40.9 | 55.2 |
| 9 | 26.3 | 8.6 | 11.5 | 1.3 | 1.1 | 1.9 | 7.8 | 40.0 | 65.8 |
| 10 | 25.0 | 4.0 | 6.2 | 3.0 | 1.6 | 1.3 | 6.8 | 45.0 | 55.6 |

TABLE 3A

| (a) | (b) | (c) | (d) | |
|---|---|---|---|---|
| 11 | 6.0 | Acetone 0.9 | Co(OAc)2 4H2O | (75) |
| 12 | 5.0 | Acetone 1.5 | Co(OAc)2 4H2O | (62.5) |
| 13 | 6.0 | n-Propanol 0.9 | Co(OAc)2 4H2O | (75) |
| 14 | 2.7 | n-Butanol 2.7 | Co(OAc)2 4H2O | (33.8) |
| Comp Test C | 3.5 +octane (1.17) | None | Co(OAc)2 4H2O | (43.8) |

TABLE 3B

| (e) | (f) | (g) | (h) | (i) | (j) | (k) | (l) | (m) | (n) |
|---|---|---|---|---|---|---|---|---|---|
| 11 | 16.1 | 7.0 | 2.0 | <1 | 2.8 | .4 | 6.3 | 39.9 | 40.4 |
| 12 | 16.3 | 9.2 | 2.1 | <1 | 2.9 | 1.2 | 5.8 | 43.0 | 37.4 |
| 13 | 16.6 | 6.5 | 2.0 | <1 | 1.9 | n-BuOH 7.4 | 40.2 | 41.3 | |
| 14 | 17.2 | 3.6 | 3.0 | <1 | <1 | n-PrOH 1.4 | 5.8 | 52.8 | 32.6 |
| Comp Test C | 6.4 | 3.1 | 6.2 | <1 | <1 | <1 | 1.5 | 36.2 | 17.7 |

TABLE 4A

| | REACTOR FEED | | | |
|---|---|---|---|---|
| Example | CH3OH (moles) | Oxygen-containing organic compound (moles) | Catalyst components (moles × 10$^{-3}$) | |
| Comp Test D | 2.0 | None | Co(OAc)2 4H2O | (25.1) |
| | | | I2 | (12.6) |
| | | | P(C6H5)3 | (43.7) |
| 15 | 1.8 | Acetone 0.15 | Co(OAc)2 4H2O | (22.5) |
| | | | I2 | (11.3) |
| | | | P(C6H5)3 | (39.3) |
| 16 | 3.0 | Acetone 2.37 | Co(OAc)2 4H2O | (37.6) |
| | | | I2 | (18.8) |
| | | | P(C6H5)3 | (65.6) |
| Comp Test E | 1.8 | None | Co(OAc)2 4H2O | (22.5) |
| | | | I2 | (11.3) |
| | | | P(C6H5)3 | (39.3) |
| 17 | 1.8 | Acetone 0.145 | Co(OAc)2 4H2O | (22.5) |
| | | | I2 | (11.3) |
| | | | P(C6H5)3 | (39.3) |

TABLE 4B

| Example | Realisable C2H5OH | Realisable CH3COOH | Dimethyl acetal * | CH3CHO | Ethers ** | n-C3H7OH + n-C4H9OH | % Molar yield CH4 + CO2 *** | % Molar selectivity to realisable C2H5OH | % MeOH conversion |
|---|---|---|---|---|---|---|---|---|---|
| Comp Test D | 24.8 | 11.1 | 5.8 | 1.5 | 1.1 | 2.2 | 13.4 | 41.7 | 59.5 |
| 15 | 30.6 | 10.9 | 7.4 | 2.0 | <1 | 2.5 | 9.8 | 48.5 | 63.1 |
| 16 | 37.8 | 12.7 | 3.6 | 2.3 | <1 | 2.4 | 5.3 | 48.8 | 77.5 |
| Comp Test E | 18.9 | 3.3 | 8.9 | 2.0 | 1.8 | 1.8 | 7.0 | 41.9 | 45.1 |
| 17 | 24.7 | 3.8 | 9.0 | 2.2 | 1.9 | 1.5 | 8.9 | 46.2 | 53.5 |

We claim:
1. A process for the production of ethanol which process comprises contacting a mixture of methanol and synthesis gas at elevated temperature and pressure with a cobalt-containing catalyst in the presence of an additive which is deliberately charged to the reaction mixture, said additive being an oxygen-containing organic compound selected from the group consisting of acetaldehyde, 1,4-dioxan, tetrahydrofuran, di-n-propyl ether, and diphenyl ether.

2. A process according to claim 1 wherein said cobalt-containing catalyst is promoted with either iodine or bromine, the molar ratio of cobalt to iodine or bromine being in the range 1:3 to 10:1.

3. A process according to claim 1 wherein said cobalt-containing catalyst is promoted with both iodine or bromine and an organo-phosphorus compound having the formula:

 (I)

wherein X is phosphorus and substituents A, B and C are individually monovalent organic radicals or any two of A, B and C together form an organic divalent cyclic ring system bonded to said X atom, the molar ratio of cobalt to compound of formula (I) being in the range of from 2:1 to 1:10 and the molar ratio of cobalt to iodine or bromine being in the range of from 1:3 to 10:1.

4. A process according to claim 3 wherein said organo-phosphorus compound of formula (I) is selected from triethylphosphine, tri-n-butylphosphine, tricyclohexylphospine, tri-t-butylphosphine and triphenylphosphine.

5. A process according to claim 1 wherein in addition to said oxygen-containing organic compound there is also charged a compound selected from the group consisting of chlorobenzene, decanoic acid, poly dimethyl siloxane fluid and methylphenyl silicone fluid, said latter compound being added in an amount such that the molar ratio of said compound to said methanol in said reaction mixture is in the range of from 30:1 to 1:10.

6. A process according to claim 1 wherein said oxygen-containing organic compound is selected from 1,4-dioxane, tetrahydrofuran, di-n-propyl ether and diphenyl ether.

7. A process according to claim 1 wherein said oxygen-containing organic compound is 1,4-dioxane.

8. A process according to claim 1 wherein said oxygen-containing organic compound is charged in an amount such that the molar ratio of said methanol to said compound is in the range from 20:1 to 1:3.

9. A process according to claim 1 wherein in addition to said oxygen-containing organic compound there is also charged to the reaction mixture a non-polar solvent selected from alkanes, benzene and alkyl-substituted benzenes.

10. A process according to claim 1 wherein in addition to said oxygen-containing organic compound there is also charged to the reaction mixture a monocarboxylic acid or a derivative thereof having the formula:

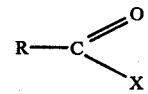 (III)

wherein the substituent R is a hydrocarbyl group or an oxygen-containing hydrocarbyl group and the substituent X is the group —OR' in which R' is independently a hydrogen atom, a hydrocarbyl group or an oxygen-containing hydrocarbyl group or X is the group —O—CO—R$^2$ wherein R$^2$ is independently a hydrocarbyl group or an oxygen-containing hydrocarbyl group, said acid or derivative thereof being added in an amount such that the molar ratio of said acid or derivative thereof to said methanol in said reaction mixture is upto 1.5:1.

11. A process according to claim 10 wherein said acid or derivative thereof is acetic acid or methyl acetate.

12. A process according to claim 1 wherein said elevated temperature is in the range 150° to 250° C., said elevated pressure is greater than 100 bar, the residence time is up to 8 hours, the molar ratio of said methanol to said synthesis gas fed is in the range of from 10:1 to 1:20, the molar ratio of carbon monoxide to hydrogen in said synthesis gas fed is in the range from 2:1 to 1:3, and the molar ratio of said cobalt to said methanol is in the range from 1:10 to 1:1000.

* * * * *

UNITED STATES PATENT AND TRADEMARK OFFICE
CERTIFICATE OF CORRECTION

PATENT NO. : 4,205,190
DATED : May 27, 1980
INVENTOR(S) : BRIAN R. GANE and DAVID G. STEWART It is certified that error appears in the above-identified patent and that said Letters Patent are hereby corrected as shown below:

Cols. 11 and 12, Table 1B, Example 7 under the heading "(k)", "1.7" should read --1.2--

Col. 11, Table 3B, Example 12, under the heading "(m)", "43.0" should read --43.6--.

Signed and Sealed this

Fifth Day of August 1980

[SEAL]

Attest:

SIDNEY A. DIAMOND

*Attesting Officer*     *Commissioner of Patents and Trademarks*